(12) United States Patent
Isogai

(10) Patent No.: US 6,588,902 B2
(45) Date of Patent: Jul. 8, 2003

(54) OPHTHALMIC APPARATUS

(75) Inventor: Naoki Isogai, Nishio (JP)

(73) Assignee: Nidek Co., Ltd., Aichi (JP)

( * ) Notice: Subject to any disclaimer, the term of this patent is extended or adjusted under 35 U.S.C. 154(b) by 15 days.

(21) Appl. No.: 09/961,349

(22) Filed: Sep. 25, 2001

(65) Prior Publication Data

US 2002/0036749 A1 Mar. 28, 2002

(30) Foreign Application Priority Data

Sep. 28, 2000 (JP) ..................................... 2000-300596

(51) Int. Cl.⁷ ................................................ A61B 3/14
(52) U.S. Cl. ..................................................... 351/208
(58) Field of Search ............................. 351/205, 206, 351/208, 211, 212, 204, 220, 221

(56) References Cited

U.S. PATENT DOCUMENTS

| | | |
|---|---|---|
| 5,463,430 A | 10/1995 | Isogai et al. |
| 5,532,772 A * | 7/1996 | Fujieda et al. ............... 351/211 |
| 5,637,109 A | 6/1997 | Sumiya |
| 5,889,576 A | 3/1999 | Fujieda |
| 5,905,562 A | 5/1999 | Isogai et al. |
| 5,907,388 A | 5/1999 | Fujieda |
| 6,079,828 A * | 6/2000 | Fujieda ....................... 351/206 |

FOREIGN PATENT DOCUMENTS

| | | |
|---|---|---|
| JP | 4-30854 B2 | 5/1992 |
| JP | 6-315465 A | 11/1994 |

\* cited by examiner

*Primary Examiner*—George Manuel
(74) *Attorney, Agent, or Firm*—Oliff & Berridge, PLC

(57) ABSTRACT

An ophthalmic apparatus provided with an ophthalmic unit for examination, measurement, or treatment, the unit having a center axis which is aligned with respect to an examinee's eye, is disclosed. This apparatus includes an observation unit through which an image of an anterior part of the examinee's eye is observed; a position detection unit which projects light to the examinee's eye and detects reflection light from the examinee's eye to obtain a position of a center of a cornea or a pupil of the examinee's eye; and a display which displays a graphic mark showing the corneal center or the pupil center with an aiming mark based on a detection result by the position detection means, the marks being superimposed on the anterior part image formed by the observation means.

12 Claims, 6 Drawing Sheets

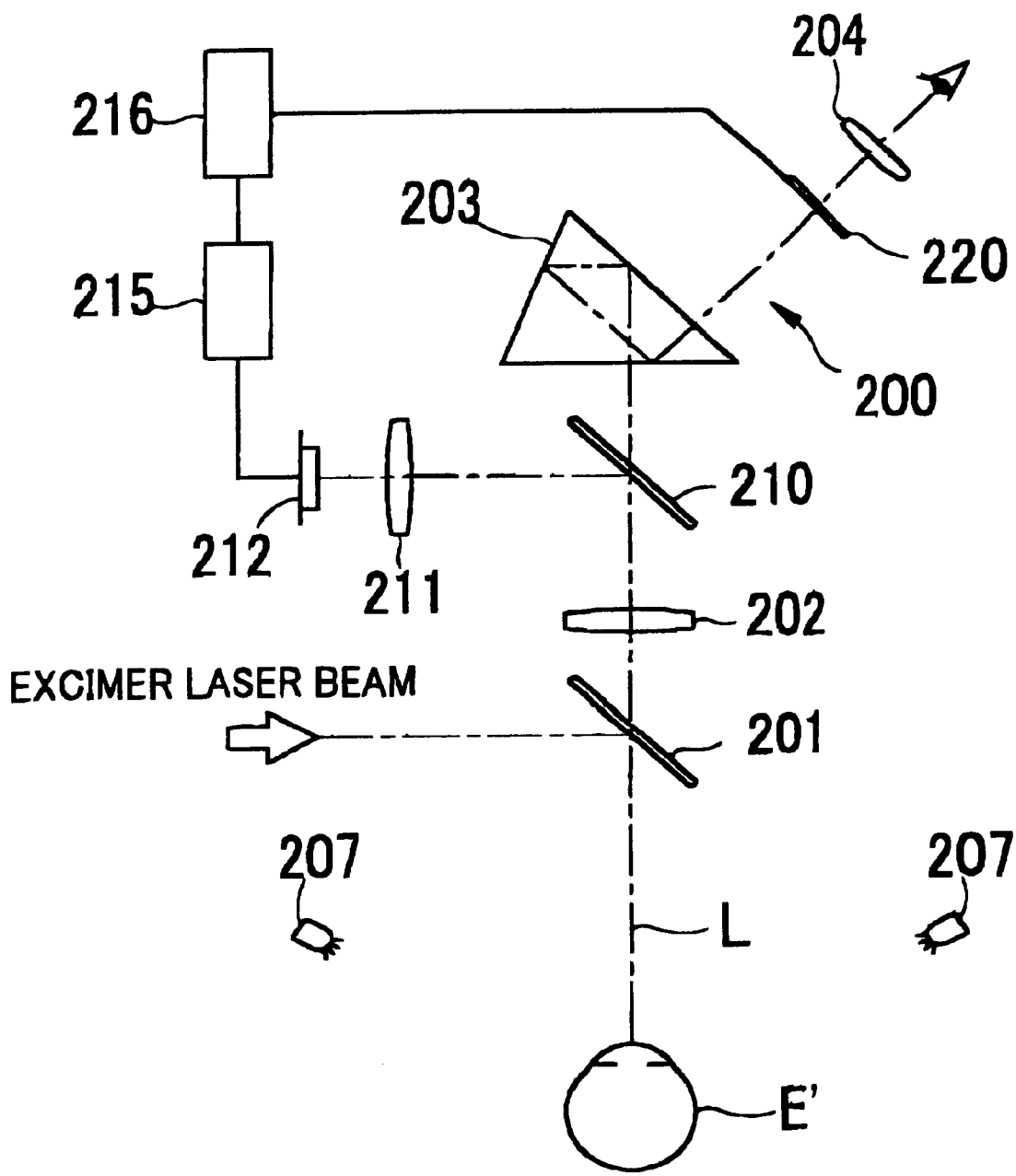

OPHTHALMIC APPARATUS

BACKGROUND OF THE INVENTION

1. Field of the Invention

The present invention relates to an ophthalmic apparatus to be used in ophthalmological clinics and others.

2. Description of Related Art

In some conventional cases, alignment (positioning) of an ophthalmic apparatus with respect to an eye to be examined is usually performed based on observation of a luminescent spot image (a reflex) formed on the center of a cornea of the examinee's eye by alignment, light projected thereon and an aiming mark. In other cases, instead of using the corneal center luminescent spot image, alignment is performed based on observation of a Mayer ring image or the shape of a pupil.

However, a conventional apparatus using the corneal center luminescent spot image has a problem that if the alignment light which forms the luminescent spot image on the corneal center is small in luminous flux width, the luminescent spot image formed on the cornea could not be visually observed until the alignment is adjusted up to a point, causing difficulty in completing the alignment. Alternatively, an ophthalmic measurement apparatus using the luminescent spot image for alignment also has the following disadvantage. When light sources for alignment are turned off in order to prevent alignment light from interfering measurement as noise light, misalignment could not be detected during the measurement.

On the other hand, the latter apparatus performing alignment with reference to the center of the Mayer ring image or the pupil center has a problem of difficulty in centering because the Mayer ring image and the pupil have no specific center to be aimed.

SUMMARY OF THE INVENTION

The present invention has been made in view of the above circumstances and has an object to overcome the above problems and to provide an ophthalmic apparatus enabling easy alignment with respect to an eye to be examined.

Additional objects and advantages of the invention will be set forth in part in the description which follows and in part will be obvious from the description, or may be learned by practice of the invention The objects and advantages of the invention may be realized and attained by means of the instrumentalities and combinations particularly pointed out in the appended claims.

To achieve the purpose of the invention, there is provided an ophthalmic apparatus provided with an ophthalmic unit for examination, measurement, or treatment, the unit having a center axis which is aligned with respect to an examinee's eye, the apparatus including: observation means through which an image of an anterior part of the examinee's eye is observed; position detection means which projects light to the examinee's eye and detects reflection light from the examinee's eye to obtain a position of a center of a cornea or a pupil of the examinee's eye; and display means which displays a graphic mark showing the corneal center or the pupil center with an aiming mark based on a detection result by the position detection means, the marks being superimposed on the anterior part image formed by the observation means.

According to another aspect of the present invention, there is provided an ophthalmic apparatus provided with an ophthalmic unit for examination, measurement, or treatment, the unit having a center axis which is aligned with respect to an examinee's eye, the apparatus including: observation means through which an image of an anterior part of the examinee's eye is observed, the observation means which includes a photographing optical system which photographs the anterior part and a display which displays the photographed anterior part image; position detection means which obtains a position of a center of a cornea of the examinee's eye, the position detection means which includes an index projection optical system which projects a first alignment index close to an optical axis of the photographing optical system and a second alignment index far from the optical axis of the photographing optical system onto the cornea of the examinee's eye, and an index detection optical system provided with a photoelectric detecting element which detects cornea reflection images of the first and second alignment indexes; and misalignment detection means which detects an apex of the cornea of the examinee's eye based on a detection result by the index detection optical system to obtain misalignment, wherein the index projection optical system projects only the second index during measurement, and the misalignment detection means obtains misalignment during measurement based on a result of detection of an image of the second index.

According to another aspect of the present invention, there is provided an ophthalmic apparatus provided with a measurement unit having a measurement optical system, the measurement optical system having a measurement optical axis which is aligned with respect to an examinee's eye, the apparatus including: position detection means which obtains a position of a center of a cornea of the examinee's eye, the position detection means which includes an index projection optical system which projects a first alignment index close to the measurement optical axis and a second alignment index far from the measurement optical axis onto the cornea of the examinee's eye, and an index detection optical system provided with a photoelectric detecting element which detects cornea reflection images of the first and second alignment indexes; and misalignment detection means which detects an apex of the cornea of the examinee's eye based on a detection result by the index detection optical system to obtain misalignment, wherein the index projection optical system projects only the second index during measurement, and the misalignment detection means obtains misalignment during measurement based on a result of detection of an image of the second index.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings,

FIG. 7 is a schematic structural view of an optical system and others in a corneal operation apparatus in a fourth embodiment.

DETAILED DESCRIPTION OF THE PREFERRED EMBODIMENTS

A detailed description of preferred embodiments of an ophthalmic apparatus embodying the present invention will now be given ref erring to the accompanying drawings.

Figure 1:
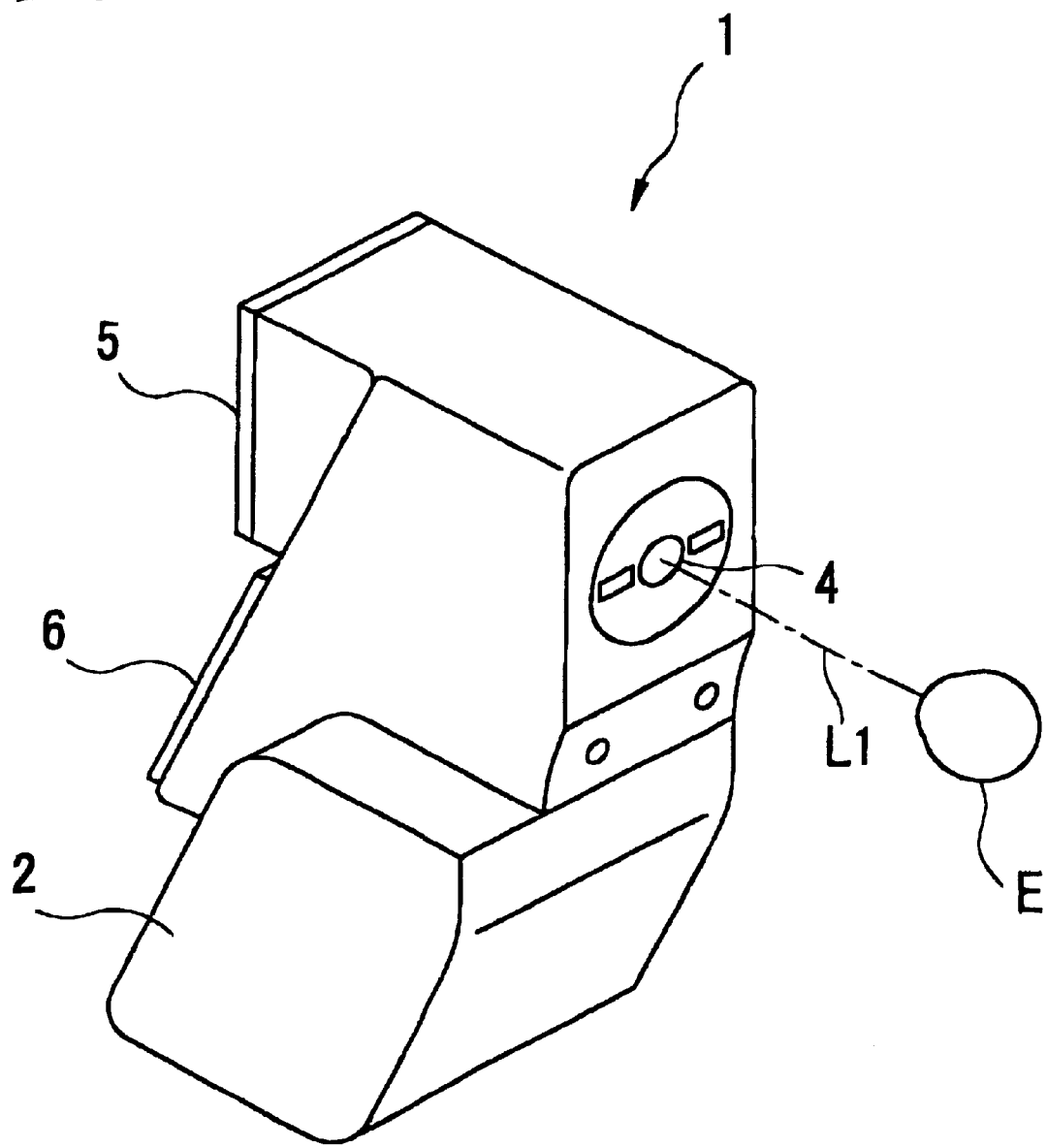
FIG. 1 is a perspective view of an objective type eye refractive power measurement apparatus in a first embodiment according to the present invention.
Figure 2:
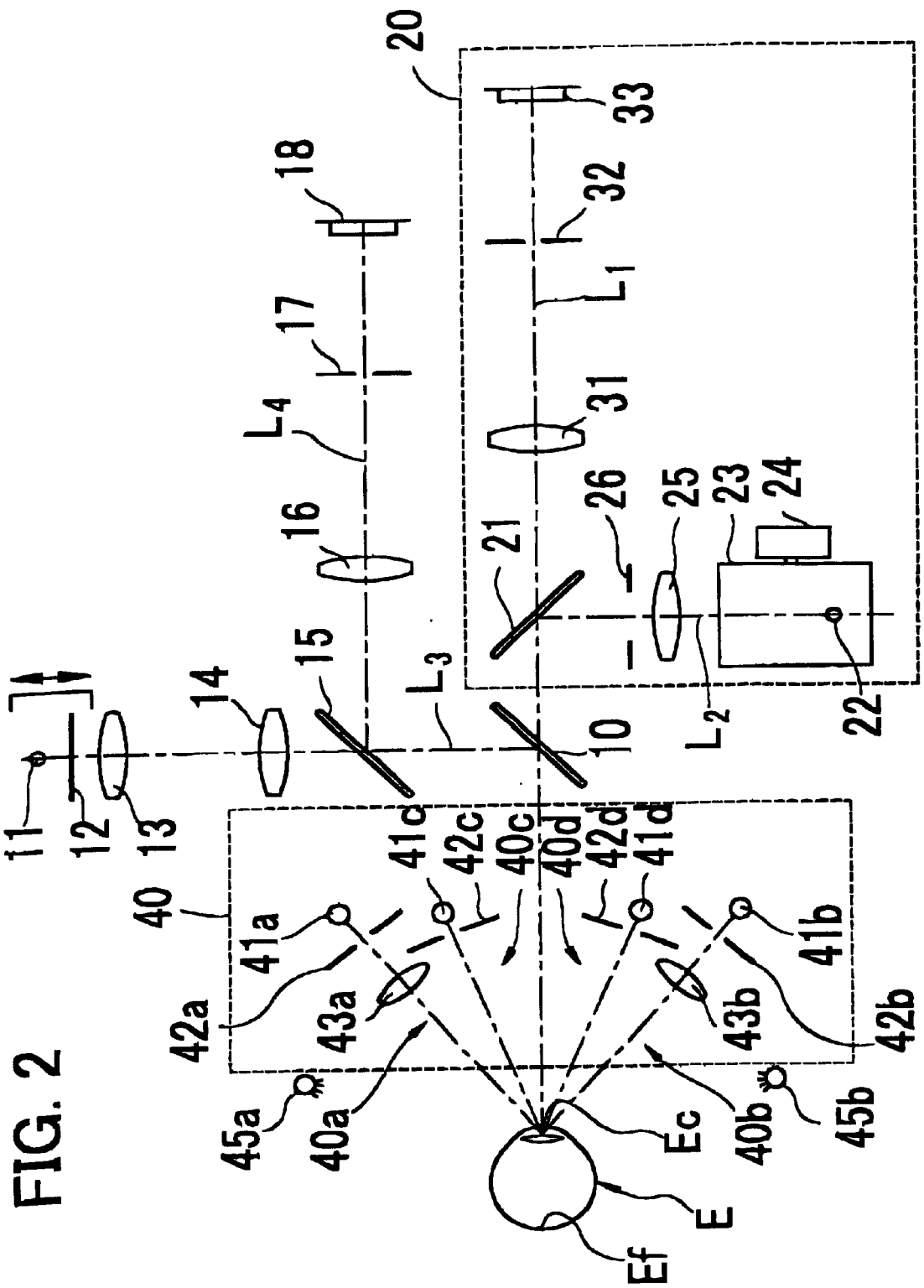
FIG. 2 is a schematic structural view of an optical system of the apparatus of FIG. 1.

FIG. 1 is a perspective view of an objective eye refractive power measurement apparatus of a hand-held type in the first embodiment. FIG. 2 is a schematic structural view of an optical system of the eye refractive power measurement apparatus shown in FIG. 1.

An apparatus 1 has a measurement window 4 on the side facing an examinee. Through the window 4, light for measurement from an eye refractive power measurement optical system 20 is projected to an examinee's eye E along a reference optical axis (measurement optical axis) L1 passing the center of the window 4. An image of an anterior part of the eye E is picked up (photographed) through the window 4. Two light sources 45a and 45b for illuminating the anterior eye part are disposed below the window 4. The apparatus 1 is also provided with an LCD monitor 5 and a switch part 6 on the side facing an examiner. The monitor 5 displays the anterior part image of the eye E, alignment information, and measurement information. The apparatus 1 is formed, in its lower part, with a holding part 2 which is hand-held by the examiner.

On the optical axis L1 which is a center axis of the apparatus positioned facing the examinee's eye E, a half mirror 10 is disposed and the measurement optical system 20 is arranged at the back of the mirror 10. The measurement optical system 20 includes a measurement light source 22 which emits infrared light for measurement, a cylindrical rotating sector 23 having slit apertures, a projection lens 25, a restricting diaphragm 26, which are arranged on an optical axis L2. This optical axis L2 is deflected by a half mirror 21 on the optical axis L1 to become coaxial with the optical axis L1. The light source 22 is disposed in an almost conjugate relationship with the vicinity of the cornea Ec of the eye E with respect to the lens 25. The sector 23 is rotated in only one direction by a motor 24 The sector 23 is formed, in the periphery thereof, with a plurality of slit apertures in each of three meridian directions of 90, 30, and 150 degrees with respect to a rotating direction of the sector 23. The measurement light Is emitted from the light source 22 illuminates the slit apertures of the sector 23. The slit-shaped measurement light is made to scan by rotation of the sector 23, passes through the lens 25 and the diaphragm 26, and is deflected by the beam splitter 21. The deflected light passes through the beam splitter 10 to be condensed on the vicinity of the cornea Ec, and projected onto a fundus Ef of the eye E.

On the optical axis L1, a light receiving lens 31, a diaphragm 32, and a light receiving section 33 are arranged, which constitute a slit image detection optical system. The diaphragm 32 is placed in a position corresponding to a rear focus point of the lens 31. The light receiving section 33 is disposed in an almost conjugate relationship with the cornea Ec with respect to the lens 31. On the light receiving section 33, three pairs of light receiving elements are located at equal intervals of 60 degrees about the optical axis L1 so that they correspond to the three meridian directions of the slit apertures of the sector 23. The light of a slit image reflected from the eye fundus Ef and passed through the pupil falls on the light receiving section 33 through the lens 31, the diaphragm 32, and others. With the three pairs of light receiving elements on the light receiving section 33, phase difference signals are obtained in correspondence to scanning directions of the slit-shaped light projected onto the eye fundus Ef, so that each refractive power in the three meridian directions can be determined. The refractive power of the eye E is thus measured. Concerning this refractive power measurement, see U.S. Pat. No. 5,907,388 corresponding to Japanese patent unexamined publication No. 10-108836.

On an optical axis L3 which is made coaxial with the optical axis L1 by the half mirror 10, there are arranged a light source 11 which emits visible light, a fixation target 12, and lenses 13 and 14, these components constituting a fixation target optical system. The light source 11 and the fixation target 12 are moved together on the optical axis L3, thereby applying fogging to the eye E. A dichroic mirror 15 is disposed between the lens 14 and the half mirror 10. On an optical axis L4 in a reflection direction by the dichroic mirror 15, there are disposed an image forming lens 16, a telecentric diaphragm 17, and a CCD camera 18 provided with an image pickup element, all of which constitute an observation optical system. This observation optical system is also used as an index image detection optical system for detecting an alignment index image.

Around the optical axis L1, an index projection optical system 40 is arranged for projecting alignment indexes used for detecting alignment state in a working distance (in a Z-direction) in addition of alignment state in up-and-down and right-and-left directions (in X- and Y-directions). The index projection optical system 40 is constructed of two led groups of first index projection optical systems 40a and 40b disposed symmetrically about the optical axis L1 and two other groups of second index projection optical systems 40c and 40d disposed symmetrically about the same axis at a smaller angle with respect to the optical axis L1 than that of the first optical systems 40a and 40b. In other words, the second optical systems 40c and 40d are disposed closer to the optical axis L1 than the first optical systems 40a and 40b. All of the optical axes of the index projection optical systems 40 intersect at the same point on the optical axis L1. The first projection optical system 40a is provided with a light source 41a which emits near-infrared light, a spot diaphragm 42a, and a collimator lens 43a, to project an index of substantially parallel flux at an infinite distance. As with the system 40a, the other first projection optical system 40b is provided with a light source 41b which emits near-infrared light, a spot diagram 42b, and a collimator lens 43b. The second projection optical system 40c includes a light source 41c which emits near-infrared light and a spot diaphragm 42c to project an index of divergent luminous flux at a finite distance. As with the system 40c, the other second system 41d includes a light source 41d and a spot diagram 42d. The alignment light (index) projected from the above projection optical system 40 forms four index images (luminescent spot images) on the cornea Ec off the center thereof. It is to be noted that the four groups of projection optical systems 40a to 40d are horizontally disposed in order to prevent the luminous flux from being eclipsed by an eyelid and eyelashes of the eye E.

Numerals 45a and 45b are light sources which emit near-infrared light for illuminating the anterior part of the eye E. These light sources 45a and 45b are arranged at the same distance and level from the optical axis L1 so as to illuminate the eye E from oblique below and in a predetermined relationship with the optical axis L1. These light sources 45a and 45b project light at a finite distance to form luminescent spot images on the cornea Ec.

Figure 3:
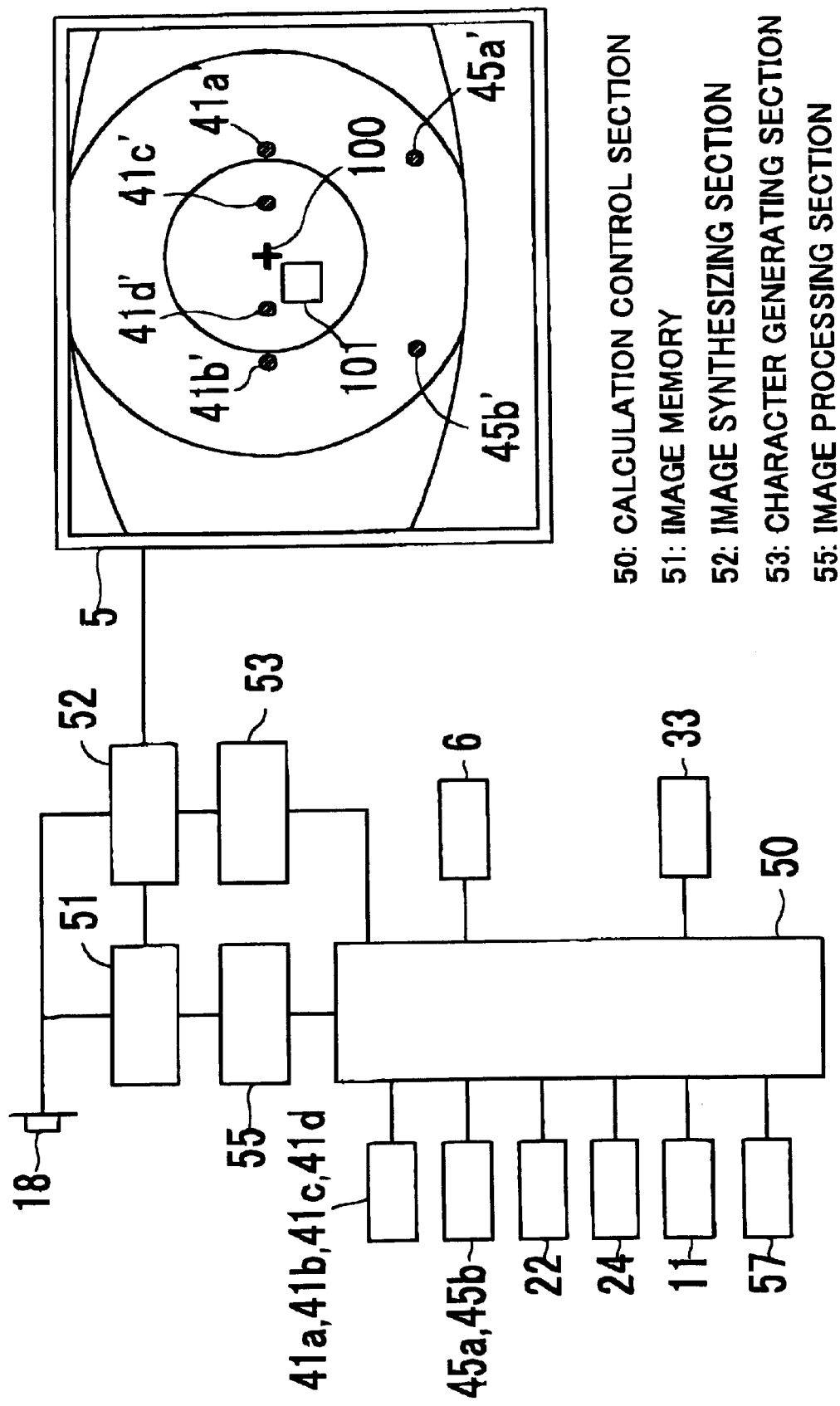
FIG. 3 is a block diagram of main parts of a control system of the apparatus of FIG. 1.

FIG. 3 is a block diagram of main parts of the control system of the apparatus. A video image output from the camera 18 is subjected to a predetermined processing and then taken in an image memory 51. The video image from the camera 18 is also displayed on the monitor 5 through an image synthesizing section 52. Numeral 53 is a character generating section which generates various characters and letters to be displayed on the monitor 5. Signals from this generating section 53 are electrically synthesized with the image signal from the camera 18 by the synthesizing section 52 and displayed on the monitor 5. Numeral 55 is an image processing section which detects signals from the image taken in the memory 51. Numeral 50 is a calculation control section which obtains the positions of the index images (luminescent spot images) from the signal detected in the processing section 55 and outputs a control signal to the generating section 53. To control eye refractive power measurement and calculate eye refractive power, the calculation control section 50 is also connected to the lay light receiving section 33, a fixation target moving section 57, and others.

With the above structure, operations of the apparatus are explained below.

The light sources 41a to 41d, 45a, and 45d are first turned on. When the apparatus is adjusted so that the window 4 faces the eye E, cornea reflection luminescent spot images and an anterior eye part image are picked up (photographed) by the camera 18 to be displayed on the monitor 5. On the screen of the monitor 5 shown in FIG. 3, numerals 41a' and 41b' show luminescent spot images formed by the first projection optical systems 40a and 40b, and other numerals 41c' and 41d'. show those by the second projection optical systems 40c and 40d. Numeral 45a' and 45b' are luminescent spot images formed by the anterior eye part illumination light sources 45a and 45b.

The image taken in the memory 51 is processed by the processing section 55. Each of the signals representative of the luminescent spot images is input in the calculation control section 50. This control section 50 determines the X and Y coordinates of each of the luminescent spot images based on the input signals, thereby detecting the corneal center (apex) as the center point between the X and Y coordinates of the luminescent spot image 41a' and those of the image 41b', both being formed by the infinite distance light, If the four luminescent spot images are detected in a line in the X direction, considering their positional relationship, the images at both ends are regarded as the luminescent spot images 41a' and 41b' formed by the first projection optical systems 40a and 40b When it determines the coordinates of the corneal center, the calculation control section 50 forms a cross-shaped mark 100 for alignment in a position corresponding to the determined coordinates on the monitor 5. The mark 100 is generated by the generating section 53, which transmits a corresponding signal to the synthesizing section 52. This section 52 electrically synthesizes the signal with the image signal from the camera 18 to display the synthesized images on the monitor 5 so that the mark 100 is superimposed on the anterior part image. When the apparatus 1 is moved in the X and Y directions, the coordinates of the luminescent spot images 41a' and 41b' vary correspondingly. The mark 100 is accordingly moved to be constantly displayed at the almost center of the cornea Ec in the anterior eye part image on the monitor 5.

At a predetermined position on the monitor 5, a square aiming mark 101 for alignment generated by the generating section 53 is displayed by electrical synthesis by the synthesizing section 52. The center of the mark 101 is used as an alignment center in the X and Y directions. To make alignment of the apparatus in the X and Y directions with respect to the eye E, the examiner moves the apparatus 1 so that the cross-shaped mark 100 is centered in the mark 101 in the same manner as the conventional alignment based on observation of the corneal center luminescent spot image.

It is to be noted that the center point between the X and Y coordinates of the luminescent spot image 41c' and those of the image 41d' may be determined as the almost center of the cornea Ec. However, the images of the finite distance light are liable to become incorrect if the corneal center largely deviates from the optical axis L1. Accordingly, the luminescent spot images 41a' and 41b' formed by the infinite distance light are preferably used as above. With the infinite distance light, as in the conventional case where the light projected from a point on the optical axis L1 forms a luminescent spot image, the examiner can easily performs alignment while observing the anterior eye part image on the monitor 5.

To detect an alignment state in the Z direction, the distance between the luminescent spot images 41a' and 41b' and the distance between the other images 41c' and 41d' are compared. This detection is made with use of the properties of the infinite light and the finite light forming the cornea reflection luminescent spot images. More specifically, if the working distance changes, the cornea reflection luminescent spot image of the infinite distance light does not change in image height, while the image of the finite distance light changes in image height. By utilizing this relation, the amount and direction of deviation of the apparatus with respect to a proper working distance is detected based on the positions of the coordinates of the luminescent spot images 41a', 41b', 41c', and 41d'. The details thereof are referred to U.S. Pat. No. 5,463,430 (corresponding to Japanese Patent Unexamined Publication No. 6-46999).

Figure 4:
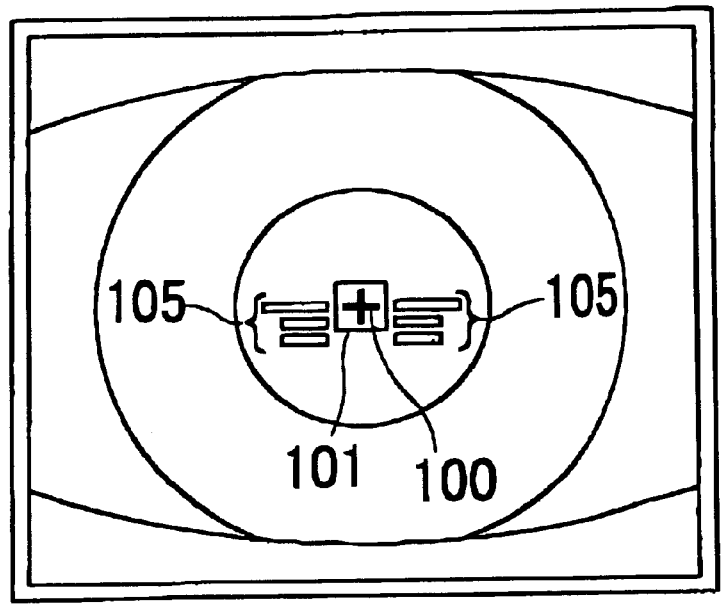
FIG. 4 is a view showing an indicator for guiding movement in a Z-direction.

Based on the detection information on the alignment in the Z direction, the calculation control section 50 causes the generating section 53 to generate and display an indicator for guiding a moving direction on the monitor 5. FIG. 4 is an example of the indicator on the monitor 5 (the luminescent spot images are omitted for making the figure easy to see). In the present embodiment, the indicator appears in the form of focus bars 105 displayed on both sides of the mark 101. If the focus bars 105 extend downward (which are illustrated in the form of three parallel bars on each side in FIG. 4), it shows that the apparatus is in a position closer to the examiner than the proper working distance. If the bars 105 extend upward, to the contrary, it shows that the apparatus is in a position closer to the examinee than the proper working distance. If the focus bars 105 appear as one bar on each side of the mark 101, it indicates that the apparatus is in a permissible range of the proper working distance.

As above, the apparatus 1 is moved so that the alignment state in each of the X, Y, and Z directions comes into a predetermined permissible range. Thereafter, the calculation control section 50 turns on the light source 22, thereby automatically starting an eye refractive power measurement. In this measurement of the eye refractive power, a preliminary measurement is first performed using phase difference signals from the three pairs of the light receiving elements on the light receiving section 33. Based on the result of the preliminary measurement, a final measurement is carried out by applying fogging by an appropriate diopter to the eye E. During this eye refractive power measurement, if the cornea reflection light of the alignment light enters the light receiving elements of the light receiving section 33, the measurement accuracy tends to be influenced by the alignment light. The light sources 41a to 41d for alignment are turned off throughout the measurement accordingly.

Because the light sources 41a to 41d are turned off during the measurement, no alignment information is obtained based on the luminescent spot images by the projection optical system 40. The mark 100 and the focus bars 105 are not also displayed. Thus, accuracy failure by misalignment can not be found during the measurement. To avoid such inconvenience, the luminescent spot images 45a' and 45b' formed by the light sources 45a and 45b are utilized. The light sources 45a and 45b continuously stay on in order to allow the examiner to observe the anterior eye part, and they are positioned far from the optical axis L1 Therefore, the measurement can be conducted with little influence by the light from the light sources 45a and 45b as compared with the case where the light sources 41a to 41d for alignment stay on.

In response to the measurement start signal, the calculation control section 50 temporarily stores the positional relation just before start of the measurement between the central coordinates between the luminescent spot images 41a' and 41b' (i.e., the detected coordinates of the corneal center) and the coordinates of the luminescent spot images 45a' and 45b'. During the measurement, the control section 50 obtains the information about the deviation of the corneal center based on variations in the positions of the luminescent spot images 45a' and 45b' and the deviation in the Z direction based on the distance between the images 45a' and 45b'. In this way, misalignment during the measurement can be judged without influence by a radius of curvature of the cornea Ec. The calculation control section 50 moves the position of the mark 100 on the monitor 5 in accordance with the information about the deviation of the corneal center and changes the appearance of the focus bars 105 in accordance with the information about the deviation in the Z direction. By viewing the monitor 5 displaying the information, the examiner can find the misalignment of the apparatus during the measurement. When the positional coordinates of the images 45a' and 45b' stored just before the measurement start change beyond the permissible range, the control section 50 determines that a measurement error occurs.

In the above embodiment, the alignment index image for detection of the corneal center is a luminescent spot image. This may be an annular index image (a Mayer ring image), which is handled as being constituted of a plurality of luminescent spot images formed by the optical systems disposed symmetrically to the optical axis L1. When the annular index image is formed on the cornea Ec, the center thereof corresponds to the almost center of the cornea Ec. The processing section 55 detects the center of the annular index image. The mark 100 is then displayed on the monitor 5 at the position corresponding to the coordinates of the detected center. With the annular index image, as above, alignment for centering can also be easily performed.

Next, a second embodiment according to the present invention is explained. The structure in the second embodiment is the same as that in the first embodiment, and different parts therefrom are mainly explained below. It is to be noted that parts identical to those in the first embodiment are indicated by the same reference numerals.

In this second embodiment, the light source 22 for measurement stays on during alignment so that the light source 22 is also used as a light source for alignment. The light source 22 projects light along the optical axis L1 to the cornea Ec, forming a corneal center luminescent spot image. In this case, the need of the projection optical systems for producing the corneal center luminescent spot image is eliminated, so that the structure of the apparatus can be simplified. However, the measurement light for eye refractive power is usually adjusted to have a small luminous flux width in order to increase measurement accuracy. As a result, the corneal center luminescent spot image could not appear until the optical axis L1 is aligned with a close vicinity of the corneal center. It is therefore difficult for the examiner to know the direction to move the apparatus until the corneal center luminescent spot image appears. Such the apparatus is poor in operability.

Figure 5:
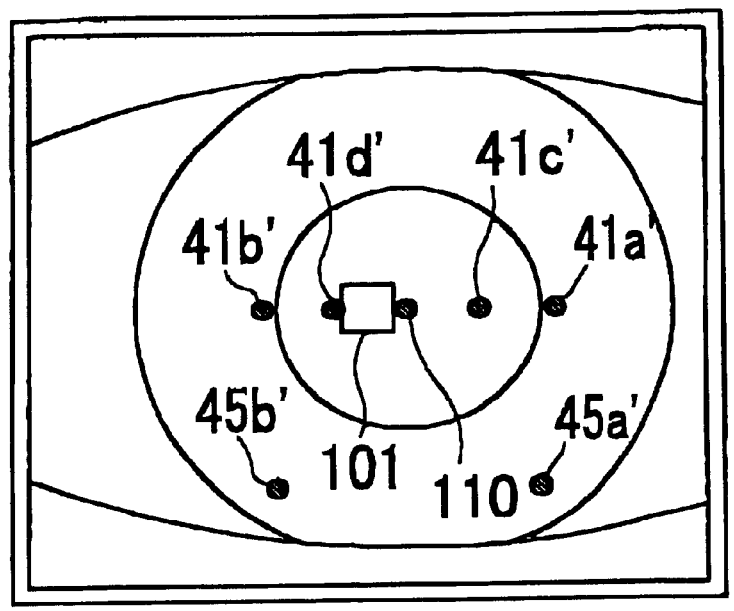
FIG. 5 is a view showing an example of a screen where a luminescent spot image appears on the center of a cornea in a second embodiment.

In the second embodiment, therefore, until the corneal center luminescent spot image can be observed on the monitor 5, the luminescent spot images 41a' and 41b' formed on or around the cornea Ec by the first projection optical systems 40a and 40b are utilized in the same way as in the first embodiment to electrically synthetically display the cross-shaped mark 100 on the monitor 5. As shown in FIG. 5, when a corneal center luminescent spot image 110 by the light source 22 comes to appear, the mark 100 is made to disappear. To be more specific, the image signal from the camera 18 is processed by the processing section 55, and the control section 50 obtains the coordinates of each of the luminescent spot images 41a' to 41d' on or around the cornea EC and the luminescent spot image 110. In view of the positional relation of the five luminescent spot images, the central image is identified as the luminescent spot image 110. The control section 50 determines whether the image 130 picked up by the camera 18 has sufficient intensity for allowing the examiner to visually identify the image 110 on the monitor 5. This intensity is judged based on a detected light quantity. If the image 110 becomes visible, the control section 50 transmits a control signal to the generating section 53 to turn off the display of the mark 100. In other words, the mark 100 is changed into a non-displayed state.

The reason why the display of the mark 100 is turned off after the luminescent spot image 110 optically formed becomes observable is as follows. Since the mark 100 is displayed based on a result of detection of the luminescent spot images on or around the cornea Ec as mentioned above, a little time lag occurs in operation. Besides, according to the accuracy of detection of the luminescent spot images, 1I there may be a case where the mark 100 deviates from the optically formed luminescent spot image 110. As a result, if the mark 100 substantially showing a false corneal center appears in addition to the luminescent spot image 110 showing a real corneal center, it would cause confusion in performing alignment. Hence the examiner makes alignment in accordance with the mark 100 until the luminescent spot image 110 appears on the monitor 5 and, after the appearance of the image 110, does alignment so as to put the image 110 in the center of the mark 101. In case that the control section 50 is unable to detect the luminescent spot image 110 due to misalignment, it displays the mark 100 again.

In the present embodiment, the mark 100 display is turned off when the luminescent spot image 110 becomes visible. In view of the fact that delicate alignment is needed near the center of aiming, the mark 100 display may be turned off after the luminescent spot image 110 enters the mark 101 or a predetermined range.

In the optical system which projects alignment light, with a large width for forming the luminescent spot image 110, similarly, the mark 100 may be displayed according to the visibility of the luminescent spot image 110 to improve the operability. More specifically, if the luminescent spot image 110 is blurry due to a large deviation of the working distance and others, alignment can be performed in accordance with the mark 100. Also in this case, the display of the mark 100 is turned off if the luminescent spot image 110 has sufficient intensity for the examiner to clearly identify. The examiner then makes alignment in accordance with the luminescent spot image 110.

A third embodiment according to the present invention is explained below. In this embodiment, alignment is performed with respect to the center of a pupil. The same components as those in the first embodiment are indicated by the same reference numerals.

Figure 6:
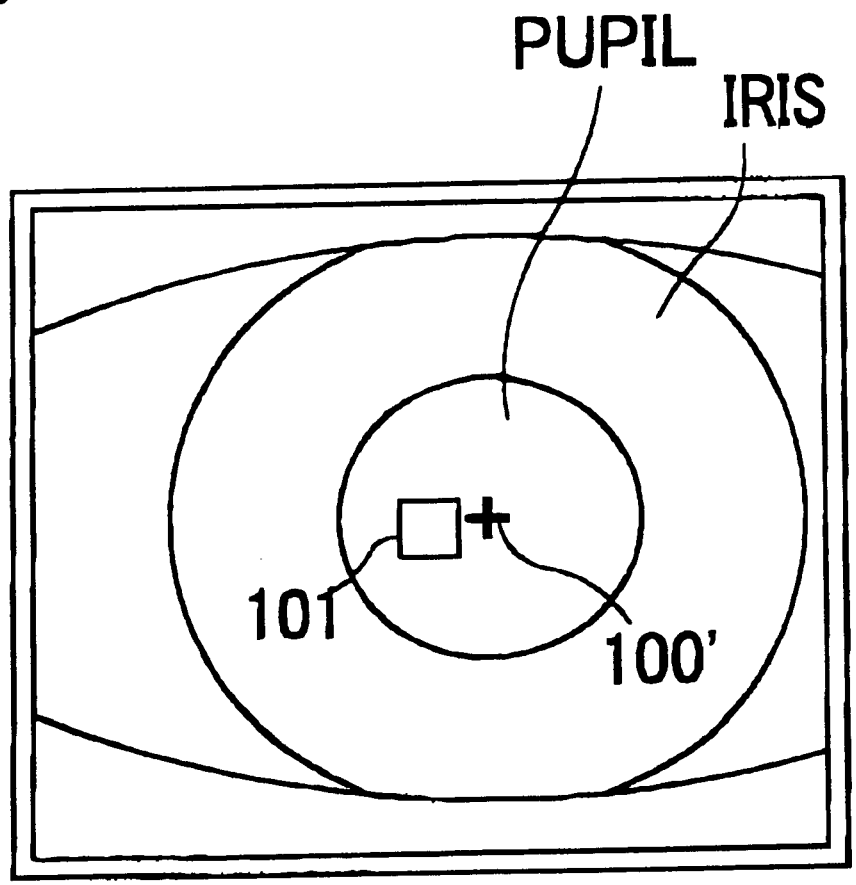
FIG. 6 is a view showing another example of a screen where a cross-shaped mark is synthetically displayed for indicating the substantial center of a pupil in a third embodiment.

An anterior eye part image picked up by the camera 18 is processed by the processing section 55 to detect the edge of the pupil. In the anterior part image, luminous intensity is different according to portions corresponding to pupil, iris, and sclera. Based on this information, the coordinates of the pupil edge can be detected. From this pupil edge detection, furthermore, the central coordinates, namely, the coordinates of the pupil center can be determined. On the monitor 5, as shown in FIG. 6, a mark 100' is electrically synthetically displayed by the generating section 53 in response to a control signal from the calculation control section 50. This mark 100' substantially shows the center of the pupil. The examiner makes alignment by moving the apparatus 1 to bring the mark 100' to the center of the mark 101. It is to be noted that the alignment in the working distance direction can be carried out with use of the luminescent spot images by the first projection optical systems 40a and 40b and the second projection optical systems 40c and 40d (not shown in FIG. 6) as in the case of the first embodiment.

For the eye refractive power measurement, the measurement light is projected into the intraocular region through the pupil. In the case where the corneal center deviates from the pupil center, the measurement light is eclipsed by the iris after the alignment utilizing the corneal center as a reference, thus disabling measurement. In this case, if alignment is performed with reference to the pupil center, measurement is enabled.

Next, a fourth embodiment according to the present invention is explained. In the fourth embodiment, as shown in FIG. 7, a transparent display 220 such as an LCD panel or the like is disposed in the observation optical path of an observation optical system. An electrically formed alignment mark is synthetically displayed with an anterior eye part image on the display 220.

FIG. 7 shows a corneal operation apparatus for irradiating the cornea with an excimer laser beam, thereby changing the radius of curvature of the cornea to correct refractive abnormality thereof. The details of this apparatus are referred to, for example, U.S. Pat. No. 5,637,109 corresponding to Japanese Patent Unexamined publication No. 6-114083. This ophthalmic apparatus is used for operation after alignment of a laser irradiation optical axis L with respect to the pupil center of a patient's (examinee's) eye E', The excimer laser beam is reflected by dichroic mirror 201 to be irradiated to the cornea of the patient's eye E', The observation optical system 200 includes an objective lens 202, a deflection-angle prism 203, and an eyepiece 204. With this optical system 200, an operator observes the anterior part of the eye E' illuminated by the light from an illumination light source 207

The image of the anterior part of the eye E' is picked up by a CCD camera 212 with an image pickup element through a beam splitter 210 and an image forming lens 211. The picked-up image is input in an image processing section 215. This processing section 215 detects the pupil center. Based on a result of detection of the pupil center, a control section 216 causes the display 220 to display a mark 100' as in FIG. 6 and controls the display position thereof. The display 220 also displays an aiming mark 101 at a predetermined position. The operator performs alignment by moving the apparatus until the mark 100' substantially representing the pupil center is centered in the mark 101.

The above way of synthetically displaying the alignment mark in the observation optical system can also be applied to any of the above first, second, and third embodiments As explained above, according to the present invention, it is possible to achieve the ophthalmic apparatus which can be easily aligned with respect to the center of a cornea or pupil.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus provided with an ophthalmic unit for examination, measurement, or treatment, the unit having a center axis which is aligned with respect to an examinee's eye, the apparatus including:

observation means through which an image of an anterior part of the examinee's eye is observed;

position detection means which projects light to the examinee's eye and detects reflection light from the examinee's eye to obtain a position of a center of a cornea or a pupil of the examinee's eye; and display means which displays a graphic mark showing the corneal center or the pupil center with an aiming mark based on a detection result by the position detection means, the marks being superimposed on the anterior part image formed by the observation means.

2. The ophthalmic apparatus according to claim 1, wherein the observation means includes a photographing optical system which photographs the anterior part and a display which displays the photographed anterior part image, the position detection means includes an index projection optical system which projects a plurality of alignment indexes onto the cornea of the examinee's eye, an index detection optical system provided with a photoelectric detecting element which detects a cornea reflection image of the alignment index, and misalignment detection means which detects an apex of the cornea of the examinee's eye based on a detection result by the index detection optical system to obtain misalignment, and the display means includes display control means which electrically synthetically displays a graphic mark showing the apex of the cornea on the display, the graphic mark being superimposed on the anterior part image.

3. The ophthalmic apparatus according to claim 2 further including:

cornea reflection image forming means which projects a light beam photographable by the photographing optical system along an optical axis of the photographing optical system to form a cornea reflection image; and detection means which detects whether the cornea reflection image photographed by the photographing optical system is in a predetermined state that an examiner can visually identify;

wherein the display control means turns off the graphic mark on the display when the cornea reflection image comes into the predetermined state that the examiner can visually identify.

4. The ophthalmic apparatus according to claim 2, wherein the index projection optical system projects only the index far from an optical axis of the photographing optical system during measurement, and the misalignment detection means obtains misalignment during measurement based on a result of detection of the corneal reflection image of the index far from the optical axis of the photographing optical system.

5. The ophthalmic apparatus according to claim 4 further including storage means which stores the result of detection of the index image far from the optical axis of the photographing optical system, wherein the misalignment detection means obtains misalignment by comparing the detection result stored in the storage means and a current position of the index image.

6. The ophthalmic apparatus according to claim 1 further including a working distance detection optical system which detects a working distance between the ophthalmic unit and the examinee's eye, wherein the display means graphically displays whether the working distance is proper.

7. The ophthalmic apparatus according to claim 1, wherein the position detection means includes an illumination optical system which illuminates the anterior part of the examinee's eye, a photographing optical system provided with a photographing element which photographs the image of the anterior part illuminated by light from the illumination optical system, and processing means which processes the anterior part image photographed by the photographing element to obtain the pupil center.

8. The ophthalmic apparatus according to claim 1, wherein the observation means includes a binocular microscopic optical system, and the display means inserts the graphic mark and the aiming mark in an optical path of the microscopic optical system.

9. An ophthalmic apparatus provided with an ophthalmic unit for examination, measurement, or treatment, the unit having a center axis which is aligned with respect to an examinee's eye, the apparatus including:

observation means through which an image of an anterior part of the examinee's eye is observed, the observation means which includes a photographing optical system which photographs the anterior part and a display which displays the photographed anterior part image;

position detection means which obtains a position of a center of a cornea of the examinee's eye, the position detection means which includes an index projection optical system which projects a first alignment index close to an optical axis of the photographing optical system and a second alignment index far from the optical axis of the photographing optical system onto the cornea of the examinee's eye, and an index detection optical system provided with a photoelectric detecting element which detects cornea reflection images of the first and second alignment indexes; and misalignment detection means which detects an apex of the cornea of the examinee's eye based on a detection result by the index detection optical system to obtain misalignment, wherein the index projection optical system projects only the second index during measurement, and the misalignment detection means obtains misalignment during measurement based on a result of detection of the corneal reflection image of the second index.

10. The ophthalmic apparatus according to claim 9, further including storage means which stores the result of detection of the second index image, wherein the misalignment detection means obtains misalignment by comparing the detection result stored in the storage means and a current position of the second index image.

11. An ophthalmic apparatus provided with a measurement unit having a measurement optical system, the measurement optical system having a measurement optical axis which is aligned with respect to an examinee's eye, the apparatus including:

position detection means which obtains a position of a center of a cornea of the examinee's eye, the position detection means which includes an index projection optical system which projects a first alignment index close to the measurement optical axis and a second alignment index far from the measurement optical axis onto the cornea of the examinee's eye, and an index detection optical system provided with a photoelectric detecting element which detects cornea reflection images of the first and second alignment indexes; and misalignment detection means which detects an apex of the cornea of the examinee's eye based on a detection result by the index detection optical system to obtain misalignment, wherein the index projection optical system projects only the second index during measurement, and the misalignment detection means obtains misalignment during measurement based on a result of detection of the corneal reflection image of the second index.

12. The ophthalmic apparatus according to claim 11, further including storage means which stores the result of detection of the second index image, wherein the misalignment detection means obtains misalignment by comparing the detection result stored in the storage means and a current position of the second index image.

* * * * *